United States Patent

Levinson et al.

[11] Patent Number: 5,813,980
[45] Date of Patent: Sep. 29, 1998

[54] FETAL PULSE OXIMETRY SENSOR WITH REMOTE SECURING MECHANISM

[75] Inventors: Mitchell Levinson, Pleasanton; Paul Mannheimer, Danville; Steven L. Nierlich; Phillip S. Palmer, both of San Leandro, all of Calif.

[73] Assignee: Nellcor Puritan Bennett Incorporated, Pleasanton, Calif.

[21] Appl. No.: 696,131

[22] Filed: Aug. 13, 1996

[51] Int. Cl.⁶ ........................................................ A61B 5/00
[52] U.S. Cl. ............................................................. 600/338
[58] Field of Search ................................... 128/633, 634, 128/664, 665, 698; 600/313, 322, 323, 338, 473, 476, 511

[56] References Cited

U.S. PATENT DOCUMENTS

| 5,247,932 | 9/1993 | Chung et al. | 128/633 |
| 5,377,675 | 1/1995 | Ruskewicz et al. | 128/634 |
| 5,497,771 | 3/1996 | Rosenheimer | 128/633 |
| 5,529,064 | 6/1996 | Rall et al. | 128/633 |

FOREIGN PATENT DOCUMENTS

| 91/07910 | 6/1991 | WIPO | 128/633 |

*Primary Examiner*—Jennifer Bahr
*Assistant Examiner*—Eric F. Winakur
*Attorney, Agent, or Firm*—Townsend and Townsend and Crew LLP

[57] ABSTRACT

A fetal pulse oximeter sensor in which a sensor head is held against the fetus by the action of a securing means which is remote from the sensor head. The securing means is sufficiently remote so that light detected by the light detector in the sensor head does not scatter through tissue which may be deformed by the securing mechanism. The securing mechanism could deform the tissue by applying pressure, to exsanguinate the tissue, or could attach to the tissue by vacuum, penetration, or glue, etc.

16 Claims, 5 Drawing Sheets

FETAL PULSE OXIMETRY SENSOR WITH REMOTE SECURING MECHANISM

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

There are two basic types of fetal sensors, presenting part sensors and beyond the presenting part sensors. "Presenting part" refers to the region of the fetus that, during labor, resides external to the cervical os. "Beyond the presenting part" falls within the uterus and extends out to the cervical os. Sensors beyond the presenting part can typically use the uterine wall to bias the sensor against the fetus. For the presenting part, however, the fetus' scalp is typically exposed to the open birth canal, and such biasing is not as readily available, with positive attachment usually being used.

Presenting Part Sensors

Known techniques for presenting part sensors include invasive attachment to fetal tissue, such as by a screw attachment penetrating the tissue, or vacuum attachment mechanisms.

Examples of presenting part sensors include U.S. Pat. No. 3,827,428 which discloses a heartbeat sensor using a coil screw for attaching to the fetus' scalp. Pulse oximeter and other sensors which use such a spiral or screw-type arrangement are also shown in U.S. Pat. Nos. 4,281,659; 4,658,825; 5,154,175; 5,361,757; 5,411,024; and German Published Application No. DE4304691A1.

Examples of vacuum-type fetal sensors include that shown in U.S. Pat. No. 4,938,218 and PCT Published Application No. WO91/15996, which shows a bellows for providing a low-pressure vacuum source. U.S. Pat. No. 4,537,197 shows another vacuum attachment fetal sensor. U.S. Pat. No. 5,497,771 uses a vacuum, but isolates the optical components.

A number of other designs are also known. U.S. Pat. No. 4,299,232 shows a combination of a suction adhesion with a suction-cup type attachment, in conjunction with an electrical pole which pierces the fetus' skin. U.S. Pat. No. 5,024,226 requires a bore hole in the brain of the patient. U.S. Pat. No. 4,543,965 uses an inflatable membrane to bias the sensor against the fetus at the presenting part.

Non-Presenting Part Sensors

Other fetal sensors are designed to go beyond the presenting part. For instance, U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. WO91/07910 uses an inflatable sac to wedge the sensor against the fetus.

The intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

A presenting part sensor is often desirable for a variety of reasons. First, it is less invasive than a beyond the presenting part sensor. Second, a presenting part sensor may be used for spot-checking saturation rather than continuous monitoring. Third, a presenting part sensor may be necessary for monitoring fetus' located high in the uterus. Fourth, a presenting part sensor is easy to place and may be more reliably attached than a beyond-the-presenting part sensor.

Another concern with fetal sensors is that the method of attachment exsanguinates the tissue immediately underneath the sensor. This limits the amount of blood encountered by the light from the sensor. In addition, mechanical attachments could provide a shunt path for the light, limiting the effectiveness of the sensor.

SUMMARY OF THE INVENTION

The present invention provides a fetal pulse oximeter sensor in which a sensor head is held against the fetus by the action of a securing means which is remote from the sensor head. The securing means is sufficiently remote so that light detected by the light detector in the sensor head does not scatter through tissue which may be deformed by the securing mechanism. The securing mechanism could deform the tissue by applying pressure, to exsanguinate the tissue, or could attach to the tissue by vacuum, penetration, or glue, etc.

The securing means may in one embodiment be positioned beyond the presenting part of the fetus, while the sensor head is biased against the presenting part of the fetus. Alternately, the positions of the sensor head and the securing means may be reversed.

In one embodiment, the securing mechanism consists of at least a pair of expandable anchors. These can be placed beyond the fetus' head where there is room to expand without contacting the uterine walls. The anchors can then be expanded, pulling on a flexible member attaching them to the sensor head, biasing the sensor head against the fetus. In one embodiment, the expandable anchors are inflatable balloons.

In another embodiment, the securing mechanism comprises a spring with a number of legs for applying a spring force to the fetus beyond the presenting part. In one embodiment, the legs extend beyond a midpoint or equator of a typical fetus' head.

In another embodiment, the securing mechanism is a spring which wedges between the fetus and the uterine wall to provide the pressure needed to hold the sensor head against the fetus, preferably at the presenting part. Preferably, the spring is pre-loaded with an amount of force sufficient for a pulse oximeter reading with minimal exsanguination of the tissue of the fetus. The spring can have a free end which is sufficiently far from the sensor head that it may simply rest in the gap between the fetus and the uterine wall, with a middle portion of the spring contacting the uterine wall to apply the necessary force.

In yet another embodiment of the present invention, the securing means is an anchoring mechanism which attaches to the fetus at a location remote from the sensor head. The anchoring mechanism can be a pre-loaded spring which may apply force to a beyond the presenting portion of the fetus, such as its cheek. This force, with the spring being pre-loaded, causes the sensor head at the presenting part to be biased against the fetus.

For a further understanding of the nature and advantages of the present invention, reference should be made to the following description taken in conjunction with the accompanying drawings.

DESCRIPTION OF THE PREFERRED EMBODIMENT

Figure 1:
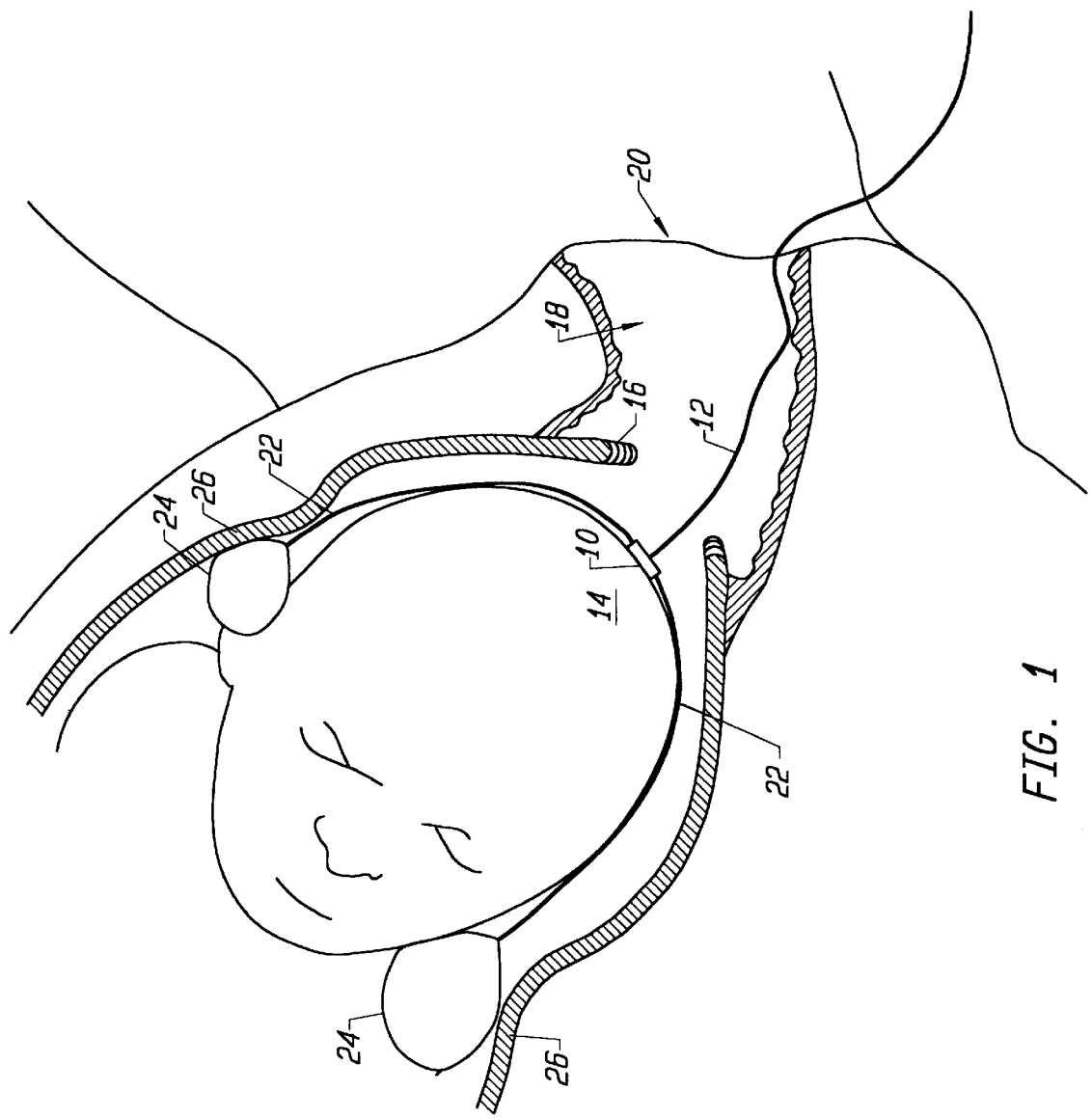
FIG. 1 is a diagram of a sensor according to one embodiment of the present invention using expandable anchors.

FIG. 1 illustrates a sensor head 10 attached to the presenting part of a fetus' scalp 14. A cord 12 connected to the sensor 10 extends past the cervix 16, through the birth canal 18 and the vagina 20.

Connected to sensor head 10 are a pair of flexible members 22. At the end of members 22 are attached expandable anchors 24. The anchors are wedged between the fetus and the uterine wall 26. Expandable member 24 could be an expanding sponge or foam, or a balloon which is inflated after insertion. The insertion could be done using a stylet or a rod to push the balloon beyond the presenting part and past the fetus' head until it is in the clear. Thereafter, it can be inflated using tubing extending through member 22 and cord 12 to the exterior. Upon inflation, the force of the balloon or foam expanding between the fetus and the uterine wall will pull on members 22, securing sensor head 10 to the fetus' head at the presenting part. Member 22 could be made of a bungee cord or other stretching material.

Figure 2:
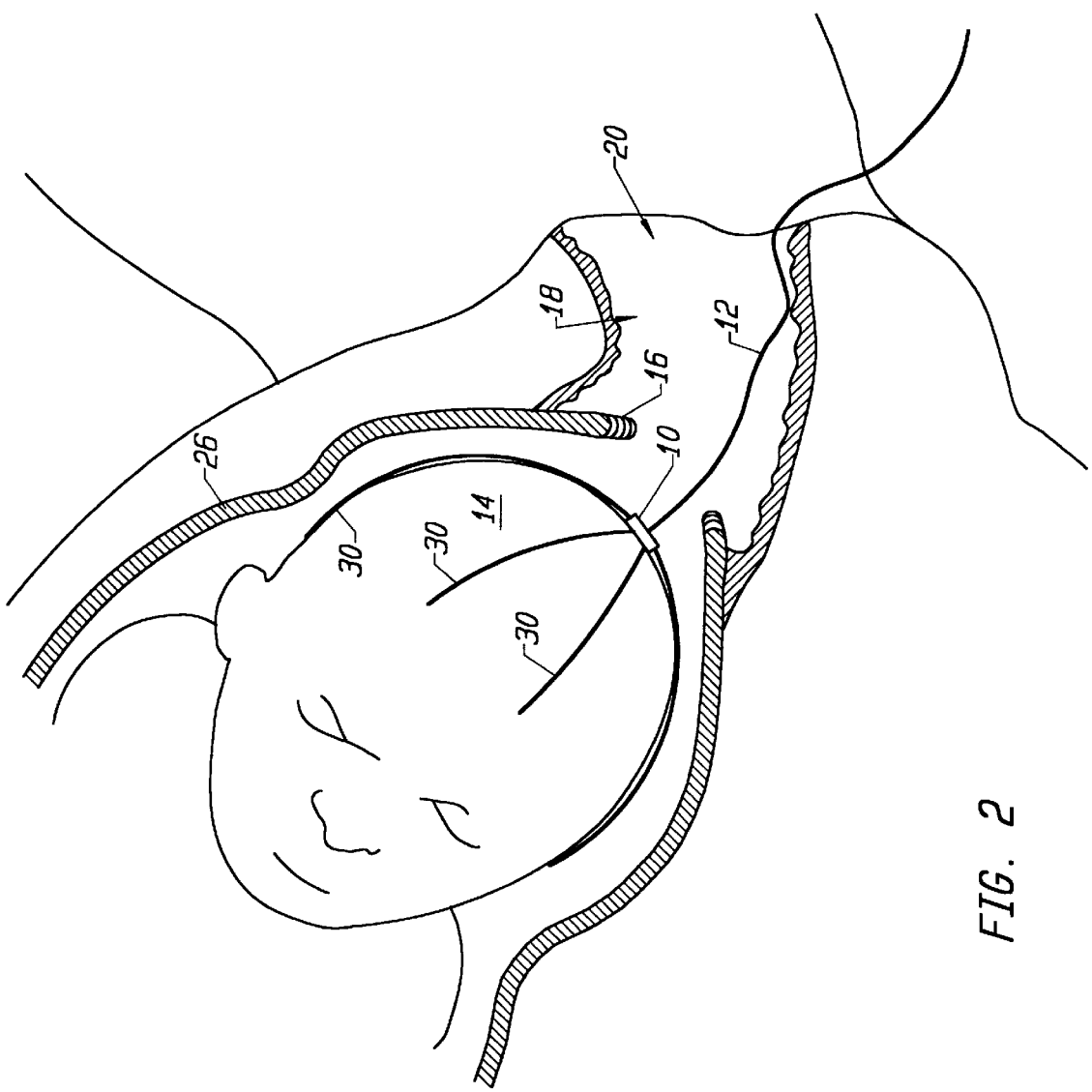
FIG. 2 is a diagram of an embodiment of a sensor of the present invention using legs for applying a spring force to the fetus beyond the presenting part.

FIG. 2 shows an alternate embodiment of the invention in which a sensor head 10 is held to the fetus' scalp 14 by a number of spring legs 30. The spring legs extend beyond an "equator" of the fetal head. In this manner, for the sensor head 10 to become dislodged, the springs would have to open up to pass back over the "equator". Preferably, the spring legs 30 are long enough to pass the equator, but not so long as to contact the fetus' eyes or other sensitive areas.

Figure 3:
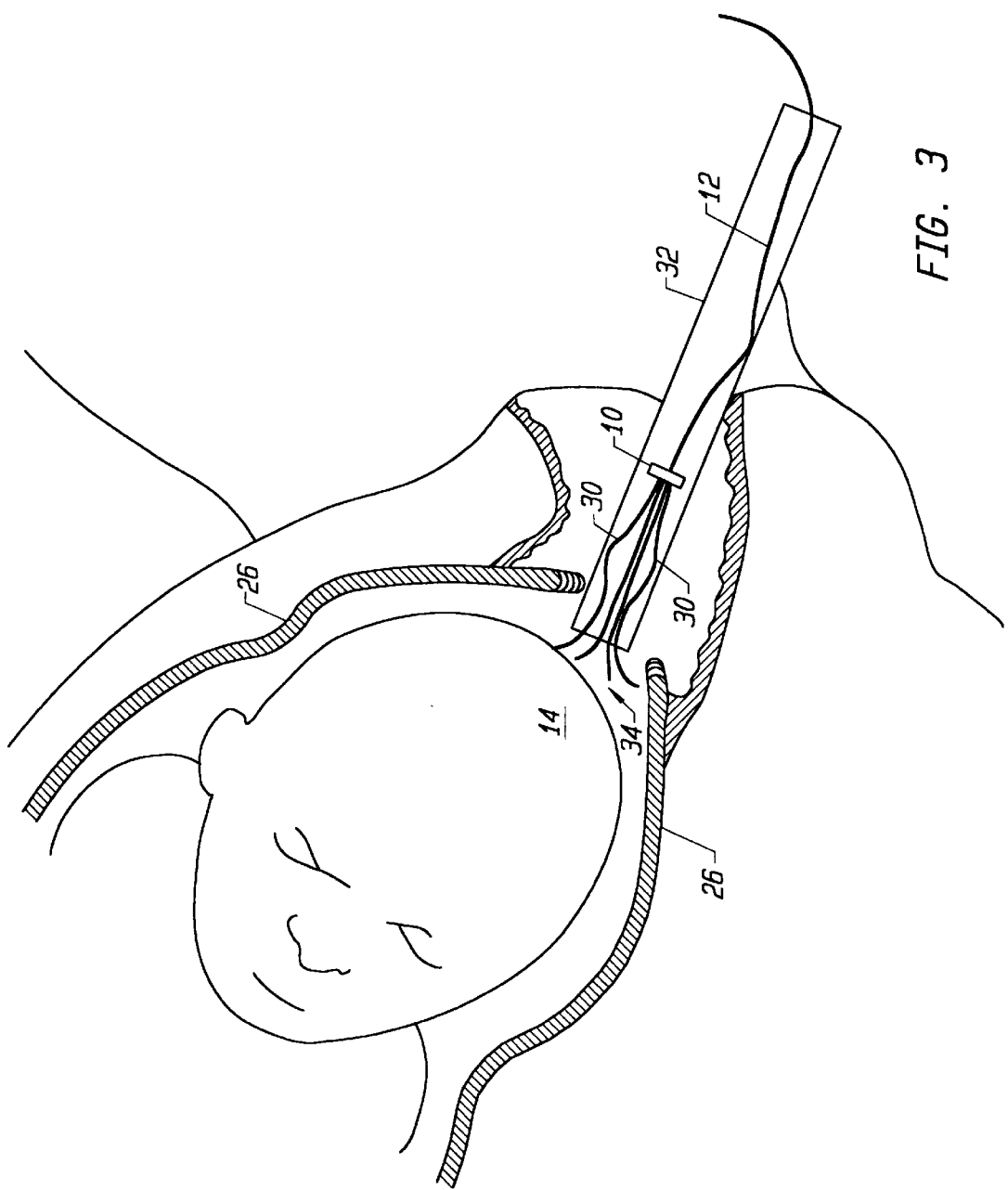
FIGS. 3 is a diagram illustrating the insertion of the sensor of FIG. 2.

FIG. 3 illustrates the insertion of the sensor in the embodiment of FIG. 2. A tube 32 is used, with the spring legs 30 being bent forward in the tube. Preferably, the springs have a relaxed, pre-stressed position which is closer to the position shown in FIG. 2. Thus, after tube 32 of FIG. 3 is removed, the spring legs 30 will expand outward, but not beyond their pre-stressed position. The widened spring legs can then be pushed around the fetus' head and will grip the fetus' head as they are expanded away from their pre-stressed position in the outward direction.

After insertion, the tube can be pulled back over cord 12, or cord 12 could wrap around the sensor head 10 and extend out of the front portion 34 of tube 32, just as spring legs 30 do. Alternately, tube 32 could have a slit along the side thin enough to allow it to pass over cord 12 after it is removed.

Figure 4:
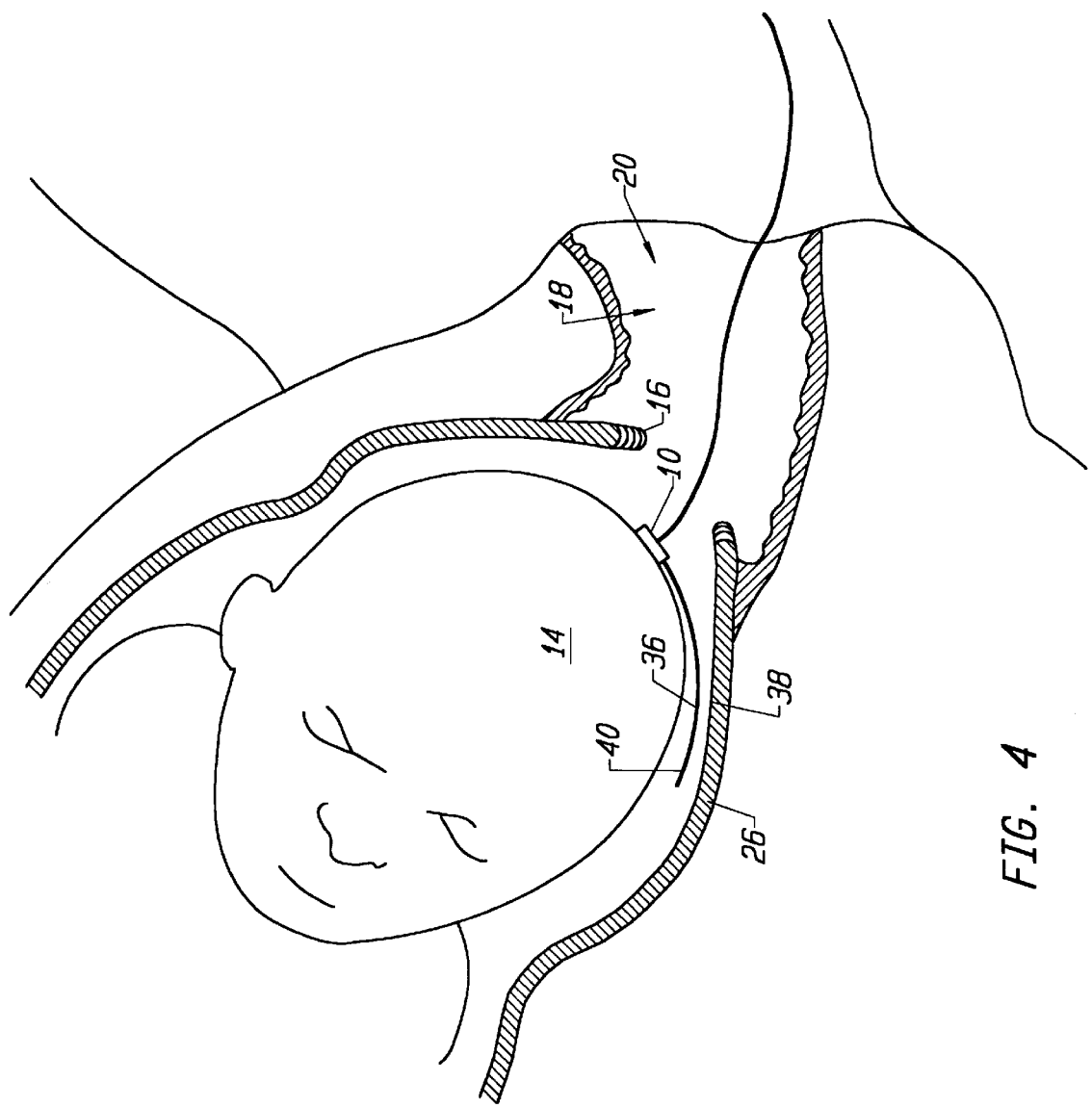
FIG. 4 is a diagram illustrating an embodiment of the invention using a pre-loaded spring wedging between the fetus and the uterine wall.

FIG. 4 shows an alternate embodiment of the present invention, in which sensor head 10 is held against the fetus 14 by a spring 36. Spring 36 can be a leaf spring, and contacts the uterine wall 26 at a point 38, where it is wedged between the uterine wall and the fetus head 14. This leaf spring preferably has a curvature which is smaller than that of the fetus' head in its normal position, such that a spring force will be applied to force sensor head 10 against the fetus' head 14. In this embodiment, the free end of spring 36 need not be in contact with either the fetus' head or the uterine wall, since it is sufficient that some portion of the leaf spring intermediate the free end 40 and sensor head 10 be in contact with the uterine wall to apply the necessary biasing force.

Figure 5:
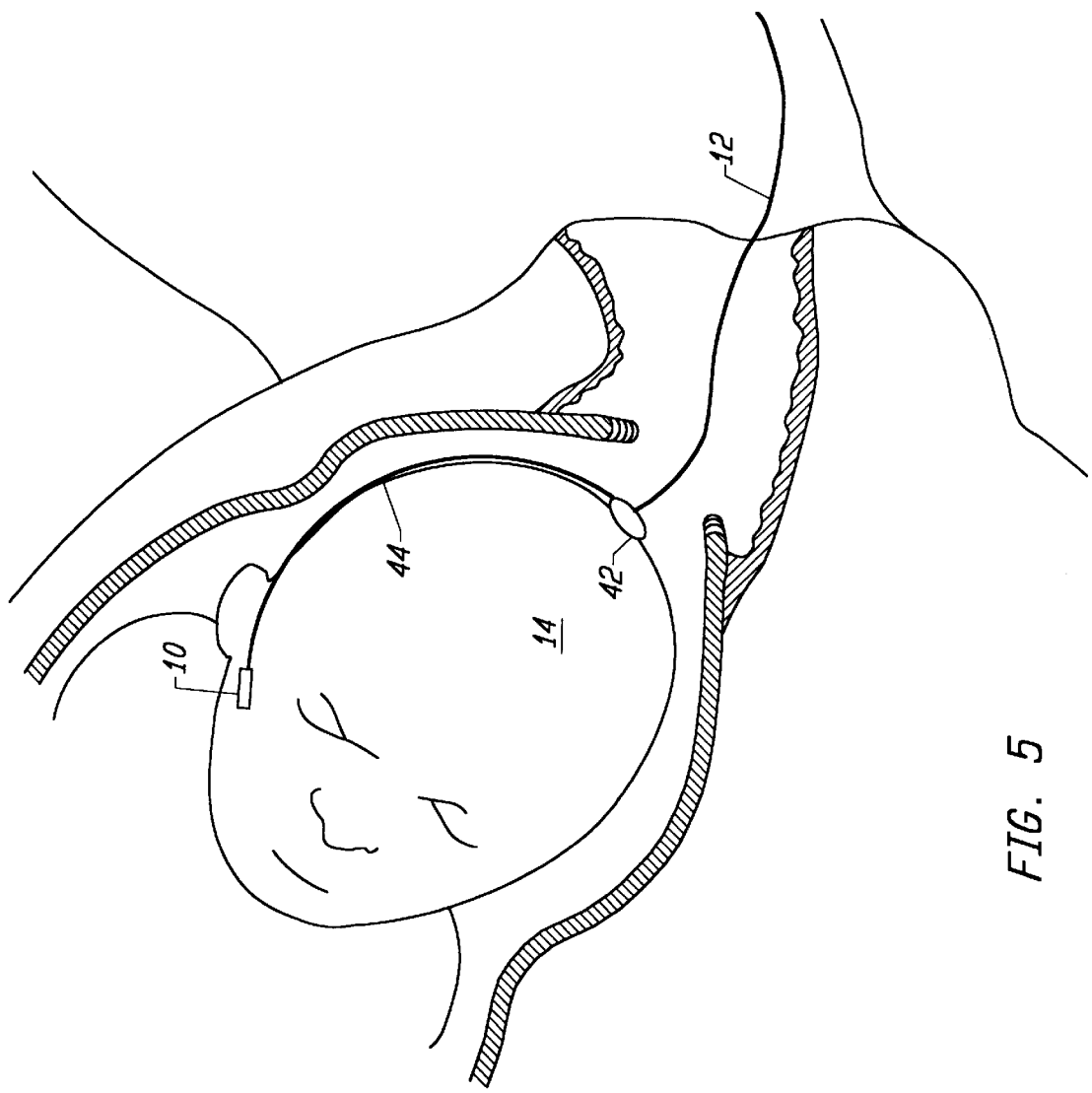
FIG. 5 is an embodiment of the present invention utilizing a spring-loaded anchor beyond the presenting part of the fetus.

FIG. 5 illustrates yet another embodiment of the present invention. In this embodiment, the sensor head 10 is placed beyond the presenting part, with an attachment mechanism 42 at the presenting part. Here, attachment mechanism 42 can simply be a pad or anchor to which a leaf spring 44 is attached, with the other end of leaf spring 44 being attached to sensor head 10. The curvature of leaf spring 44 in the relaxed position is smaller than that of a typical fetus' head, so that force will be applied to bias sensor head 10 against the fetus. As in other embodiments, a cord 12 provides the electrical signals to and from sensor head 10, and passes through or alongside the spring 44. Spring 44 could be a leaf spring inside of a plastic enclosure, which also encloses the electrical cords. Alternately, a fiberoptic cable could be used instead of an electrical cord, with the emitter and detector outside of the mother.

Anchor 42 preferably has a size, shape and consistency to provide an anchoring function. In one embodiment, it may be a soft rubber which conforms to the shape of the fetus' head 14, and provides a gripping or non-sliding action through a series of small ridges. In addition, it may have a slightly curved shape to conform to the shape of the fetus' head. Anchor 42 may consist of a suction cup, held in place by its concave shape. Alternately, anchor 42 may consist of a vacuum attachment or a spiral or hook electrode, or an adhesive.

Figure 6:
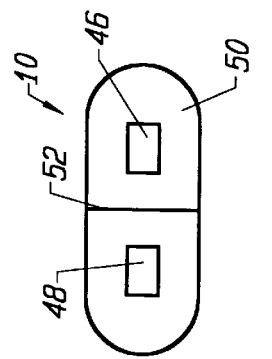
FIG. 6 is a diagram of a sensor head used in the embodiments of FIGS. 1–5.

FIG. 6 illustrates a sensor head 10 used in the embodiment of FIGS. 1 through 5. The sensor head may include a light emitter 46 and a light detector 48. The sensor body 50 may be made of a soft plastic or rubber-like material which conforms to the fetus' head. Alternately, it may be made of a relatively rigid material. If made of a rigid material, a light barrier 52 may be included to prevent shunting which may occur between the emitter and detector if the sensor head is not pliable enough to conform to the fetus' head completely.

Each of the embodiments shown in FIGS. 1–5 share the feature that the tissue-deforming sensor securing means is remote from the location of sensor 10. Light detected by the light detector in the sensor head does not scatter through the tissue which may be deformed by the securing mechanism.

Multiple embodiments of sensor 10 could be utilized, as is well-known in the art. For instance, the emitter and detector may have bumps molded over them and a transparent window, such as shown in U.S. Pat. No. 5,099,842. These bumps would provide a scrubbing effect to allow the sensor to be moved and positioned against the fetus' head, pushing its way through hair and other solids which may impede direct contact with the fetus' scalp. Alternately, optical fibers may be substituted for either or both of the emitter and detector so that these components may be located remotely from the sensor head.

As will be understood by those of skill in the art, the present invention may be embodied in other specific forms without departing from the spirit or essential characteristics thereof. For example, the tube of FIG. 3 need not be used, with a hand holding the springs instead for insertion. Alternately, in the embodiment of FIG. 5, the position of the anchor and the sensor may be reversed or otherwise varied. Accordingly, the embodiments are merely illustrative of the present invention, and reference should be made to the appended claims which set forth the scope of the invention.

What is claimed is:

1. A perinatal pulse oximeter sensor for application to a fetus and providing a signal corresponding to blood oxygen saturation, comprising:

a sensor head having a fetus engaging surface for engagement with said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and securing means, coupled to said sensor head, for securing said sensor head to said fetus at a remote location of said fetus, said remote location being sufficiently removed from said sensor head so that said detected light doesn't scatter through tissue of said fetus deformed by said securing means in a sufficient amount to affect said measurement of blood oxygen saturation;

wherein said securing means biases said sensor head against a presenting part of said fetus, and said securing means is positioned to contact said fetus beyond the presenting part.

2. The perinatal sensor of claim 1 wherein said securing means comprises first and second expandable anchors coupled by elongate members to opposite sides of said sensor head.

3. The perinatal sensor of claim 2 wherein said expandable anchors are inflatable balloons.

4. The perinatal sensor of claim 1 wherein said securing means comprises an anchoring member for attaching to said fetus at a location remote from said sensor head.

5. A perinatal pulse oximeter sensor for application to a fetus and providing a signal corresponding to blood oxygen saturation, comprising:

a sensor head having a fetus engaging surface for engagement with the presenting part of said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and securing means, coupled to said sensor head, for securing said sensor head to said fetus at a remote location of said fetus beyond the presenting part by applying pressure to said fetus at said remote location, said remote location being sufficiently removed from said sensor head so that said detected light at the presenting part of said fetus doesn't scatter through tissue of said fetus deformed by said securing means in a sufficient amount to affect said measurement of blood oxygen saturation.

6. A perinatal pulse oximeter sensor for application to a fetus and providing a signal corresponding to blood oxygen saturation, comprising:

a sensor head having a fetus engaging surface for engagement with said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and securing means, coupled to said sensor head, for securing said sensor head to said fetus at a remote location of said fetus, including first and second expandable anchors coupled by elongate members to opposite sides of said sensor head, said remote location being sufficiently removed from said sensor head so that said detected light doesn't scatter through tissue of said fetus deformed by said securing means in a sufficient amount to affect said measurement of blood oxygen saturation.

7. The perinatal sensor of claim 6 wherein said expandable anchors are inflatable balloons.

8. A perinatal pulse oximeter sensor for application to a fetus and providing a signal corresponding to blood oxygen saturation, comprising:

a sensor head having a fetus engaging surface for engagement with said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and securing means, coupled to said sensor head, for securing said sensor head to said fetus at a remote location of said fetus, said remote location being sufficiently removed from said sensor head so that said detected light doesn't scatter through tissue of said fetus deformed by said securing means in a sufficient amount to affect said measurement of blood oxygen saturation, said securing means including
a plurality of legs for applying a spring force to said fetus beyond said presenting part.

9. The perinatal sensor of claim 8 wherein said legs extend beyond a mid-point of a typical fetus scalp.

10. A perinatal pulse oximeter sensor for application to a fetus and providing a signal corresponding to blood oxygen saturation, comprising:

a sensor head having a fetus engaging surface for engagement with said fetus beyond the presenting part of said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and securing means, coupled to said sensor head, for securing said sensor head to said fetus, said securing means applying pressure to said fetus at said presenting part of said fetus sufficiently removed from said sensor head so that said detected light beyond the presenting part of said fetus doesn't scatter through tissue of said fetus deformed by said securing means in a sufficient amount to affect said measurement of blood oxygen saturation.

11. The perinatal sensor of claim 10 wherein said securing means comprises first and second expandable anchors coupled by elongate members to opposite sides of said sensor head.

12. The perinatal sensor of claim 10 wherein said securing means comprises a spring having a first end coupled to said sensor head and a second portion adapted for wedging between said fetus and a uterine wall.

13. The perinatal sensor of claim 10 wherein said securing means comprises means for applying a vacuum to said fetus.

14. The perinatal sensor of claim 10 wherein said securing means comprises means for penetrating the tissue of said fetus.

15. The perinatal sensor of claim 10 wherein said securing means includes an adhesive.

16. A perinatal pulse oximeter sensor for application to a fetus and providing a signal corresponding to blood oxygen saturation, comprising:

a sensor head having a fetus engaging surface for engagement with said fetus beyond the presenting part of said fetus;

a light emitter connected to said sensor head and positioned to emit light of at least two wavelengths directed at said fetus;

a light detector mounted in said sensor head at a position to detect said light scattered through tissue of said fetus, said light detector providing said signal corresponding to blood oxygen saturation; and an anchor, coupled to said sensor head, said anchor being separated from said sensor head sufficiently to apply pressure to said fetus at said presenting part of said fetus so that said detected light beyond the presenting part of said fetus doesn't scatter through tissue of said fetus deformed by said anchor in a sufficient amount to affect said measurement of blood oxygen saturation.

\* \* \* \* \*